United States Patent
Kohl

(10) Patent No.: US 8,858,457 B2
(45) Date of Patent: Oct. 14, 2014

(54) METHOD AND DEVICE FOR THE AUTOMATIC EVALUATION AND ANALYSIS OF A CAPNOGRAM AND COMPUTER PROGRAM FOR IMPLEMENTING THE METHOD AS WELL AS COMPUTER PROGRAM PRODUCT WITH SUCH A COMPUTER PROGRAM

(75) Inventor: Hans-Joachim Kohl, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 606 days.

(21) Appl. No.: 13/079,335

(22) Filed: Apr. 4, 2011

(65) Prior Publication Data

US 2012/0083707 A1 Apr. 5, 2012

(30) Foreign Application Priority Data

Oct. 5, 2010 (DE) .......................... 10 2010 047 546

(51) Int. Cl.
| | |
|---|---|
| *A61B 5/091* | (2006.01) |
| *A61B 5/08* | (2006.01) |
| *A61B 5/083* | (2006.01) |
| *G06F 19/00* | (2011.01) |

(52) U.S. Cl.
CPC .............. *G06F 19/345* (2013.01); *A61B 5/091* (2013.01); *A61B 5/0836* (2013.01)
USPC ............................ 600/532; 600/529; 600/538

(58) Field of Classification Search
USPC ............................ 600/529–543; 128/204.23
See application file for complete search history.

(56) References Cited

U.S. PATENT DOCUMENTS

| | | | |
|---|---|---|---|
| 7,885,771 B2 * | 2/2011 | Roecker et al. | 702/24 |
| 2007/0068528 A1 * | 3/2007 | Bohm et al. | 128/204.23 |
| 2008/0114551 A1 * | 5/2008 | Roecker | 702/24 |
| 2008/0300500 A1 * | 12/2008 | Reisfeld | 600/532 |
| 2010/0101577 A1 * | 4/2010 | Kaestle et al. | 128/204.22 |

FOREIGN PATENT DOCUMENTS

EP 1 579 882 A1 9/2005

OTHER PUBLICATIONS

Baker et al. "Alterations in ventilatory pattern and ratio of dead-space to tidal volume." Chest. Dec. 1987;92(6):1013-7.*
Shalhout, B. "Clinical Measurements: A Quick Guide to Capnography." Philips Medical Systems. Sep. 2004.*
Tusman et al. "Model fitting of volumetric capnograms improves calculations of airway dead space and slope of phase III." J Clin Monit Comput. Aug. 2009;23(4):197-206. Epub Jun. 11, 2009.*
Grevenstein et al. "Clinical Perspectives." Capnography: Clinical Aspects: Carbon Dioxide Over Time and Volume, 1st Edition. : Cambridge University Press, 2004, pp. 3-12.*

(Continued)

*Primary Examiner* — Navin Natnithithadha
*Assistant Examiner* — Meredith Weare
(74) *Attorney, Agent, or Firm* — McGlew and Tuttle, P.C.

(57) ABSTRACT

A method implemented, e.g., as software and a device operating according to the method for the automatic evaluation and analysis of a capnogram are provided. Measured values for an expired volume—volume measured values—and measured values for a carbon dioxide concentration—concentration measured values—are recorded for the breathing gas of a test subject. An automatic approximation of at least one part of the curve of the concentration measured values over the volume measured values is performed, by using three mutually adjacent straight lines for the approximation. The area is determined using the third straight line according to Fowler for the determination of the serial dead space Vds.

10 Claims, 6 Drawing Sheets

(56) References Cited

OTHER PUBLICATIONS

Fowler W.S., "Lung Function Studies. II. The Respiratory Dead Space", Am. J. Physiol., vol. 154 (1948), pp. 405-416), Philadelphia, PA, USA.

Gerado Tusman et al., Model fitting of columetric capnograms improves calculations of airway dead space and slope of phase III, Journal of Clinical Monitoring and Computing, vol. 23, No. 4, pp. 197-206, Jun. 11, 2009.

* cited by examiner

METHOD AND DEVICE FOR THE AUTOMATIC EVALUATION AND ANALYSIS OF A CAPNOGRAM AND COMPUTER PROGRAM FOR IMPLEMENTING THE METHOD AS WELL AS COMPUTER PROGRAM PRODUCT WITH SUCH A COMPUTER PROGRAM

CROSS-REFERENCE TO RELATED APPLICATIONS

This application claims the benefit of priority under 35 U.S.C. §119 of German Patent Application DE 10 2010 047 546.7 filed Oct. 5, 2010, the entire contents of which are incorporated herein by reference.

FIELD OF THE INVENTION

The present invention pertains to a method for the automatic evaluation and/or analysis of a so-called capnogram, especially a volume capnogram, as well as to a corresponding device, which is provided and suitable for automatically carrying out the method. Any device in which the investigation of respiration or of the lung function of a test subject or patient plays a role, i.e., for example, an anesthesia apparatus or a respirator, may be considered for use as such a device. While a respirator partly or temporarily assists the breathing of a test subject or patient, hereinafter globally called test subject, other devices, e.g., capnometers, are intended essentially, without such an active function, essentially for analytical purposes, e.g., for non-invasive methods for supporting a diagnosis especially of pathological changes of the lungs or for the observation of therapeutic results in the treatment of the lungs, etc. All devices of the above-mentioned type will be summed up here and below under the term device or apparatus. Implementation as software is considered for the method, so that the present invention also pertains to a corresponding computer program and to a computer program product with such a computer program.

BACKGROUND OF THE INVENTION

Representation of a so-called volume capnogram is common in prior-art respirators to enable the caregivers to assess the breathing process, for example, in case of such a device used in intensive care.

FIG. 1 shows such a volume capnogram as an example.

To obtain such a volume capnogram, measured values for an indicator of an expired volume and measured values for an indicator of a carbon dioxide concentration—$CO_2$ concentration for short—are recorded for the breathing gas of a test subject. For example, a quantity of air flow that can be measured with a flow sensor may be used as an indicator of an expired volume. For example, the actual $CO_2$ concentration ($F_{CO2}$) itself or a $CO_2$ partial pressure ($P_{CO2}$) may be used as the indicator of a $CO_2$ concentration. A $CO_2$ sensor may be used to measure the $CO_2$ concentration. The measured values are usually recorded at preset or presettable, normally equidistant points in time, so that a plurality of value pairs are obtained.

Two measured values each, recorded at the same time or at least essentially at the same time, form a value pair. The recorded measured values are measured values for an indicator of a carbon dioxide concentration, hereinafter called concentration measured values for short, and measured values for an indicator of the expired volume, hereinafter correspondingly called volume measured values for short. Each value pair correspondingly comprises a concentration measured value and a volume measured value. A linear curve is obtained by the graphic representation of the measured values recorded during an expiration process in a Cartesian system of coordinates, namely, when representing the concentration measured values over the corresponding volume measured values, and the entirety of the measured values thus represented forms the volume capnogram. The volume measured values are plotted on the abscissa and the concentration measured values on the ordinate.

The volume capnogram recognizably has three sections, which are called phase 1, phase 2 and phase 3, beginning from the left, in the scientific literature, and are designated by P1, P2 and P3 in FIG. 1.

At the beginning of expiration, breathing gas (gas), which has not participated in the gas exchange with the blood, reaches from the airways the respective sensor, e.g., the $CO_2$ sensor. It correspondingly contains only a small percentage of or no $CO_2$ (phase 1). The measurable $CO_2$ concentration increases appreciably (phase 2) only when gas from the alveoli of the lungs reaches the $CO_2$ sensor. The $CO_2$ concentration reaches a plateau at the end of the rise phase, and the $CO_2$ concentration normally continues to rise at least slightly even within the plateau (phase 3).

Two parameters are of special significance in the evaluation of the capnogram: On the one hand, the volume beginning from which the $CO_2$ concentration rises and, on the other hand, the change in the $CO_2$ concentration in the area of the plateau.

The volume beginning from which the $CO_2$ concentration rises describes the expired quantity of gas, which has not reached the alveoli and could not therefore participate in the gas exchange with the blood. At least the gas content in the mouth, pharynx and upper part of the trachea of the test subject belongs to this quantity of gas. There is no gas exchange in this tidal volume area via the alveoli. The $CO_2$ concentration will consequently correspond essentially to the $CO_2$ concentration in the air inspired previously. This volume is called a serial dead space or, after subtracting the gas volume of the measuring device, also anatomic dead space. It is designated by the symbol Vds in the literature. The dead space or a change in the dead space during a therapy or during a longer-lasting observation of a test subject can be used as an indication of changes in the lungs or airways.

The change in the $CO_2$ concentration in the area of the plateau is quite generally an indicator of the quality of the gas exchange in the lungs.

The method according to Fowler (Fowler W. S., Lung function studies II: The respiratory dead space, *Am. J. Physiol.*, Vol. 154 (1948), pp. 405-416) has come commonly into use and is frequently used for the determination of these two parameters.

The measured value curve in FIG. 1 is also called $FCO_2$ curve for the further explanation, because the measured value curve represents the carbon dioxide concentration ($F_{CO2}$) during the expiration process, i.e., over the volume measured values. Fowler's method begins by drawing a straight line through the plateau of the $FCO_2$ curve in phase 3 "with the naked eye." A vertical line is subsequently positioned in the course of the $FCO_2$ curve in phase 2. The position of the vertical line is selected to be such that an area to the left of the vertical line and an area to the right of the vertical line are equal or at least approximately equal. The area being considered here to the right of the vertical line is defined, on the one hand, by the line itself, then the $FCO_2$ curve and finally the straight line drawn through the plateau. The area to the left of the vertical line is likewise defined by the line itself and the $FCO_2$ curve as well as the abscissa of the system of coordinates ($FCO_2$ zero line). FIG. 2 shows this fact graphically. The two areas to the left and right of the vertical line are designated by A1 and A2, respectively, in the diagram. Such an evaluation has been performed so far only by medical staff trained in this field based on an examination of the capnogram, and the position of the vertical line was essentially estimated in light of the equality of the areas adjoining on the right and left. An actual determination of the contents of the two areas adjoining on the right and left and hence an exact positioning of the vertical line to determine the serial dead space has been performed essentially for scientific publications and the like.

An automatic evaluation of a volume capnogram, called an expirogram there, has become known from DE 10 2004 039 194 A. Reference is made to this document to avoid repetitions that are unneeded here, e.g., in respect to the explanation of some technical terms such as "dead space" or generally in respect to the explanation of the physiological principles of gas exchange in the lungs.

The approach from DE 10 2004 039 194 A uses a certain type of function, which comes close to an ideal capnogram. Such an approach is not flexible enough to identify capnograms that considerably differ therefrom and are hence unusable without human interaction.

SUMMARY OF THE INVENTION

The object of the present invention is to provide a sufficiently flexible method for the automatic evaluation of a volume capnogram, which both determines the straight line to be provided for the Fowler algorithm through phase 3 and is capable of identifying unusable capnograms.

This object is accomplished according to the present invention with a method with the following method steps provided for this in a method for automatically evaluating and analyzing a capnogram, e.g., in a method for operating a respirator or generally in a method for operating a device for the analysis of breathing and/or the lung function: Measured values for an indicator of an expired volume and measured values for an indicator of a carbon dioxide concentration are recorded for the breathing gas of a test subject. The measured values for an indicator of the carbon dioxide concentration and the measured values for an indicator of the expired volume are called here and hereinafter concentration measured values and volume measured values for short. A curve of the concentration measured values over the volume measured value forms a basis for an automatic analysis of the measured values recorded with the following additional steps: An automatic approximation of the curve of the concentration measured values over the volume measured values is performed by means of three sections of the straight line.

A computer-implemented, numerical optimization algorithm, e.g., the Levenberg-Marquardt algorithm, which is known to be a numerical optimization algorithm for solving nonlinear compensation problems by means of the least squares method, may be used for the automatic approximation of at least part of the curve describing the concentration measured values over the volume measured values. The least squares method is known per se as a standard mathematical method for compensation calculation and is used in the Levenberg-Marquardt algorithm to evaluate the progression of optimization. In general, a curve, which extends as close as possible to the points of the point set, is sought for a point set preset by measured values. The point set preset by measured values in the problem being considered here is represented by the individual points of the capnogram, and the approximation is performed such that six parameters are determined, comprising an initial concentration value F0, a first and second value pairs (V1, F1), (V2, F2), and a final concentration value F3. Together with the fixed initial and final volume values V0 and V3, these parameters define three straight lines, which adjoin each other and by means of which the capnogram is approximated, the first value pair defining the end point of the first section and the starting point of the second section and the second value pair defining the end point of the second section and the starting point of the third section.

Based on the parameters determined, an indicator for the serial dead space of the lungs of the test subject is determined corresponding to Fowler's method as an automatic analysis of the recorded measured values.

The above-mentioned object is also accomplished with a device for carrying out the method. A respirator or any other apparatus, which assists respiration or is intended for breathing analysis or the like, especially a capnometer, may be used as a device. The device may also be comprised as an essentially separate functional unit of an apparatus having further functions. A respirator may in turn be used as such an apparatus comprising the device as a functional unit.

The advantage of the present invention is that the underlying approach makes possible a simple implementation of the above-described method and possibly also embodiments thereof, which will be explained below. This analogously also applies to the creation of a device or apparatus, which device or apparatus carries out the method, operates according to the method or is intended for carrying out the method.

Advantageous embodiments of the present invention are provided.

The indicator of the serial dead space of the lungs of the test subject can be automatically estimated in an especially simple manner on the basis of a distance between the volume measured values belonging to the first and second value pairs, e.g., by taking the mean of the two volume measured values as an indicator of the serial dead space. If the volume measured values of the first and second value pairs are designated symbolically by V1 and V2, respectively, a numerical value is obtained as an indicator of the serial dead space—symbol Vds—in the form of $$Vds=V1+(V2-V1)/2=(V2+V1)/2.$$

The automatically determined indicator of the serial dead space of the lungs of the test subject can be automatically improved iteratively according to Fowler. The value determined at first for the serial dead space and then the value determined newly stepwise for the serial dead space are shifted for this to the right or left in the system of coordinates until a first area and a second area before and after the determined value agree. The first and second area being considered here before and after the determined value are the areas also considered in Fowler's method and reference is therefore made to their representation in FIG. 2. The iterative improvement begins with a value located, e.g., in the middle between the two volume measured values belonging to the first and second value pairs as an initial indicator of the serial dead space. The contents of the two areas A1 and A2 are determined for this value. We then advance in the direction of the larger area measured point by measured point and the area contents are determined anew. The small area is now enlarged and the larger area reduced. The procedure stops when the measured point at which the smaller area becomes the larger one is reached. The area between this and the preceding measured point can finally be divided into A1 and A2 by interpolation, so that equality is achieved. The volume thus determined is the sought value Vds.

Based on the second value pair and another, last value pair, with a final volume measured value and a corresponding concentration measured value, an indicator can be determined for the quality of a gas exchange in the lungs of the test subject. It is known that the increase in the concentration measured values in the area of the plateau in phase 3 of the capnogram is an indicator of the quality of gas exchange in the lungs. The increase in the concentration measured values in the area of the plateau in phase 3 can be expressed as follows with the second value pair and last value pair and the volume and respective concentration measured values comprised thereby, here and hereinafter symbolically designated by V2 and F2 as well as V3 and F3:

$$dFCO_2/dV=(F3-F2)/(V3-V2).$$

An estimation of the quality of the approximation and/or an estimation of the usability of the measured values recorded can be automatically performed on the basis of the first and second value pairs and the last value pair. For example, the fact that an actual value is below a preset or presettable threshold value for a difference of the final volume measured value V3 and the volume measured value V2 belonging to the second value pair can be automatically evaluated as lack of usability of the measured values. Such an evaluation can relate, as in the preceding example, to the second and last value pairs only. On the other hand, the evaluation may also relate to the first and second value pairs or to the second value pair and the last value pair by comparing, e.g., the slopes of the straight lines extending between them, i.e., of the straight lines in phase 2 and phase 3 of the capnogram. Permissible relations are defined and suitably made available for such a comparison, i.e., stored, e.g., in a memory, and the automatic evaluation as a lack of quality of the approximation or lack of usability of the measured value can be made contingent upon whether the range of permissible relations thus defined is abandoned. Further criteria can be derived from a comparison of the length of phase 3 with values for, e.g., V3 or Vds, etc.

An exemplary embodiment of the present invention will be explained below on the basis of the drawings. Objects or elements corresponding to each other are designated by the same reference numbers in all figures.

The exemplary embodiment shall not be construed to represent a limitation of the present invention. Variations and modifications are rather possible within the framework of the present disclosure, which the person skilled in the art can find, for example, by combining or modifying individual features or process steps that are described in conjunction with the general or special specification part and are contained in the claims and/or drawings for accomplishing the object and which can lead to a new object or to new process steps or sequences of process steps by means of features that can be combined. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
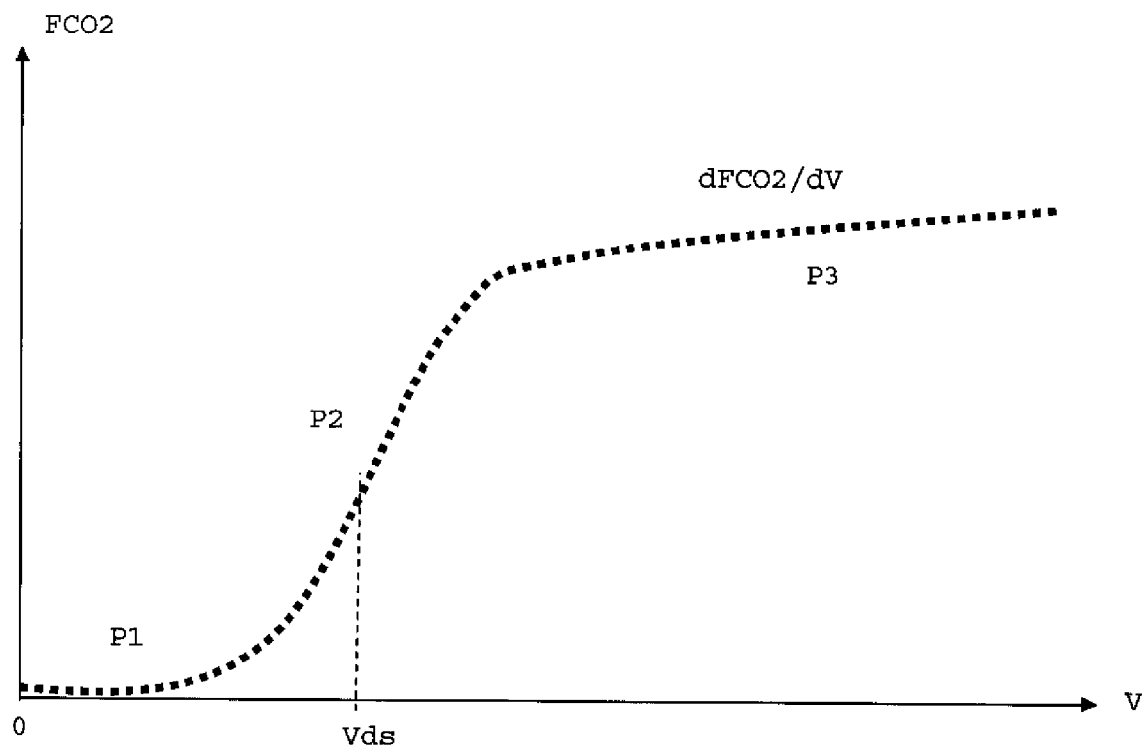
FIG. 1 is a graph showing a so-called volume capnogram, i.e., a curve of measured values here, which represent a $CO_2$ concentration in the expired breathing air, over measured values for the expired gas volume.

Referring to the drawings in particular, FIG. 1 shows, as was mentioned already, a curve of measured values, which represent a $CO_2$ concentration in the expired breathing air, over measured values for the expired gas volume. The representation of the measured values, as is shown in FIG. 1, is called a volume capnogram. The measured values for the $CO_2$ concentration—concentration measured values (e.g., symbolically designated by $F_k, F_{k+1}, F_{k+2}, \ldots F_{k+n}$, wherein k to k+n are scanning times for recording the measured values) are plotted in the Cartesian system of coordinates shown as $FCO_2$ along the ordinate. The measured values for the expired gas volume—volume measured values (e.g., analogously to the above at the concentration measured values, symbolically designated by $V_k, V_{k+1}, V_{k+2}, \ldots V_{k+n}$)—are plotted as V along the abscissa. The curve describing the measured values is called the $FCO_2$ curve, and three sections or phases P1, P2, P3 are recognizable in this. Important parameters of the $FCO_2$ curve are an indicator of the serial dead space, symbolically designated as Vds, approximately in the middle of the second phase P2 and a slope $dFCO_2/dV$ of the third phase P3.

Figure 2:
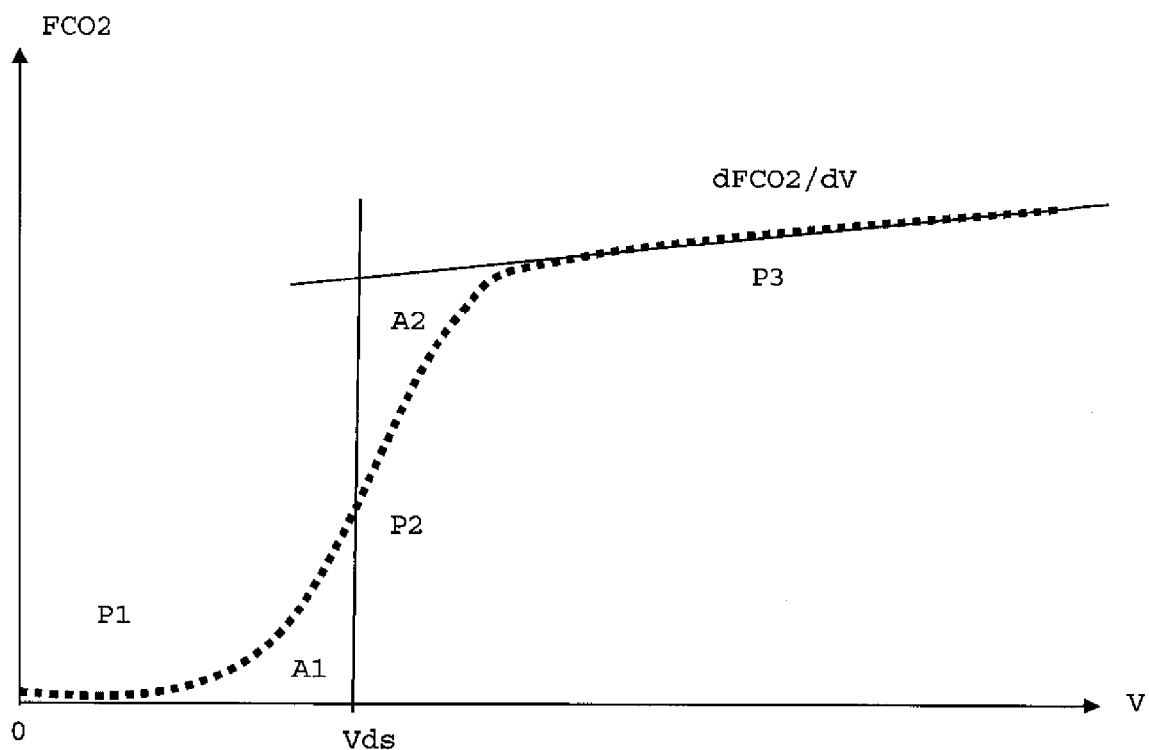
FIG. 2 is a graph showing the capnogram from FIG. 1 with two straight lines fitted into same for evaluating the capnogram according to Fowler's method.

FIG. 2 shows, as was also mentioned already, the approach for determining the above-mentioned parameters with Fowler's method (Fowler W. S., Lung function studies II: The respiratory dead space, *Am. J. Physiol.*, Vol. 154 (1948), pp. 405-416). A first straight line is fitted for this to the $FCO_2$ curve in the area of the third phase 3 and a vertical line is subsequently drawn into the area of the second phase P2 such that the contents of the areas A1, A2 defined to the right and left by the vertical line and the $FCO_2$ line are equal or at least essentially equal.

Figure 3:
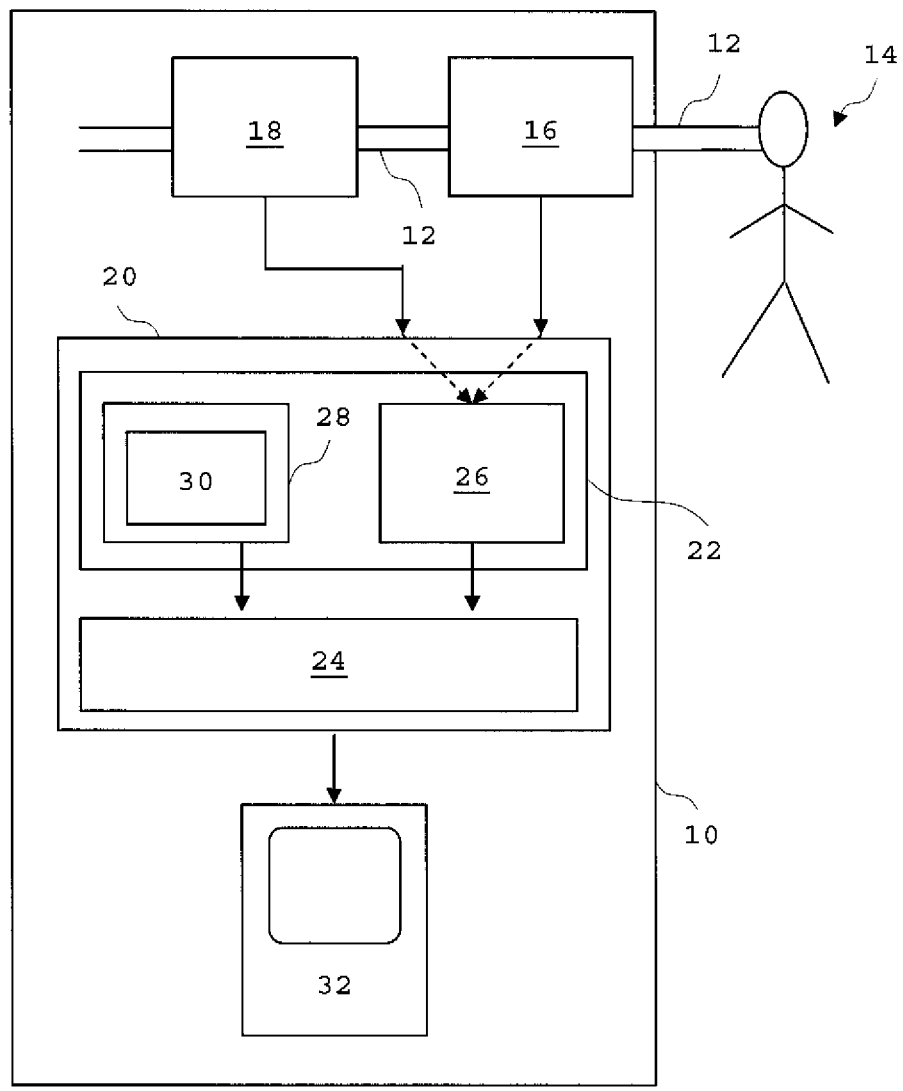
FIG. 3 is a schematically simplified view of a device for the automatic evaluation and analysis of a capnogram.

FIG. 3 schematically shows in a simplified form a device 10 for the automatic determination of at least one of the above-mentioned two parameters. A respirator or an apparatus of the above-described type may be used as the device 10. Such an apparatus or a respirator may also comprise the device 10 as a functional unit. A modular design of the device 10 may also be considered in the latter case, so that the device can be combined with existing apparatuses in order to expand the range of functions thereof.

Breathing air expired by a test subject 14 flows into a line unit 12, which is comprised either by the device 10 or an apparatus comprising the device 10. If the device 10 is used in a respirator, the test subject 14 is supplied, depending on the embodiment of the respirator, via the line unit 12 with a breathing gas enriched especially with oxygen. The gas expired by the test subject 14 reaches, at any rate, a first sensor for detecting volume measured values, e.g., a flow sensor 16, which measures the volume flow (flow), and a second sensor for detecting concentration measured values, e.g., a $CO_2$ sensor 18, which measures the $CO_2$ concentration or $CO_2$ partial pressure. The order in which the sensors 16, 18 are arranged is freely selectable and the concentration measured values can be equally recorded in the line unit 12 before the volume measured value or at about the same site in the line unit 12. Both sensors 16, 18 send the respective measured values recorded to an analysis unit 20 of device 10. Sensors 16, 18 may be part of the device 10 or part of an apparatus comprising the device 10. In the latter case, the device comprises means, i.e., for example, an interface, for taking over the measured values from the sensors 16, 18. At least one memory 22 and a processing unit 24 in the manner of a microprocessor or the like belong to the device 10. Measured values entered from the sensors 16, 18 are stored in a data storage area 26 of memory 22. The function of the analysis unit 20 is determined by a computer program stored in a program memory area 28 of the memory 22, which is called a control program 30 here. The reception and storage of the volume and concentration measured values sent by the sensors 16, 18 in the data storage area 26 take place under the control of the control program 30. Furthermore, evaluation and analysis of the measured values thus stored take place under the control of the control program 30. As a result of the evaluation/analysis, at least one indicator of the serial dead space of the lungs of the test subject 14 is shown on a display unit, e.g., an optical display device in the manner of a display screen 32. As an alternative or in addition, an indicator of the quality of the gas exchange in the lungs of the test subject 14 is displayed. The values displayed or possibly displayed are the values determined for Vds and $dFCO_2/dV$. The display unit may be part of the device 10 or of the apparatus comprising said device or may be arranged externally from same or arranged at said device or apparatus and connected to said device or apparatus in a communicating manner.

Figure 4:
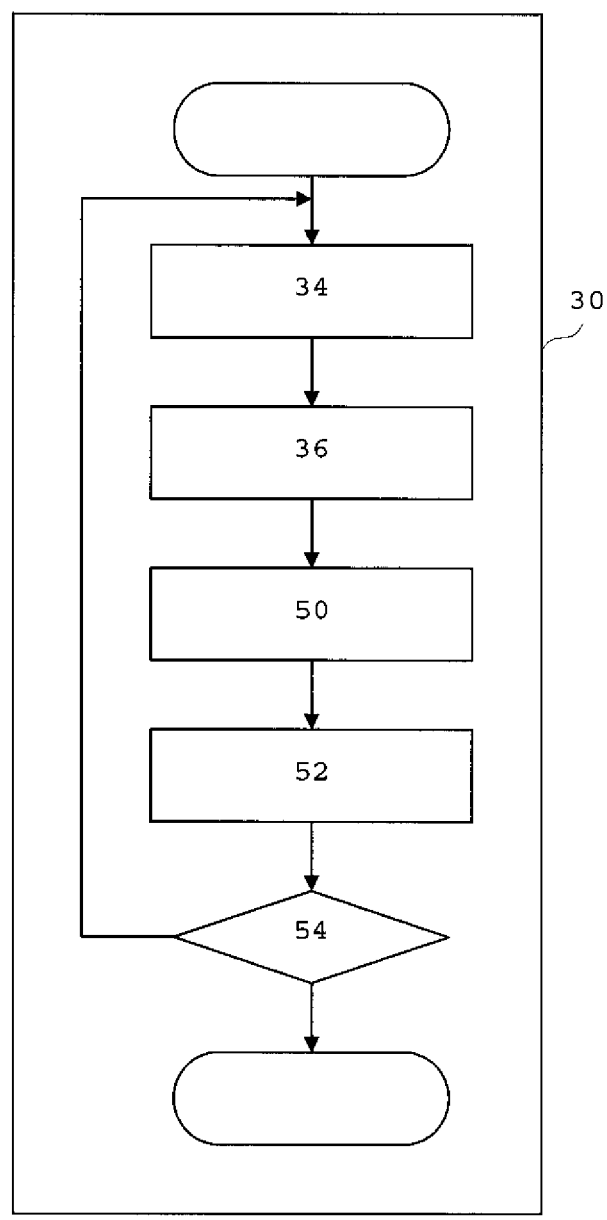
FIG. 4 is a simplified flow chart of a control program, under the control of which the automatic evaluation and analysis of a capnogram is carried out.

FIG. 4 graphically shows individual aspects of the control program 30 (FIG. 3) on the basis of a flow chart.

Control program 30 comprises a first program code block 34 with at least one program code instruction for receiving the measured values, namely, the concentration and volume measured values, whose graphic representation was already shown in FIG. 1 and FIG. 2. The first program code block 34 comprises program code instructions to recognize the beginning and end of an expiration process by the test subject 14 (FIG. 3), so that a sequence of recorded measured values can be exactly assigned to an expiration process. The beginning and end of an expiration process can be recognized, for example, from a reversal of the sign of the volume measured value, because an expiration process follows an inspiration process and another inspiration process follows an expiration process. Possibilities of recognizing the beginning and end of an expiration process are known per se. The reversal of the sign of the volume measured values is mentioned here only as an example. The first program code block is executed until all the measured values belonging to an expiration process are received and stored in the data storage area 26 of memory 22 of the analysis unit 20.

The analysis of the measured values received is then performed. A second program code block 36 is provided herefor. This comprises, e.g., a computer-implemented Levenberg-Marquardt algorithm, which is known per se. The algorithm is provided to determine three straight lines, which describe the curve of the concentration measured values recorded over the volume measured value recorded, i.e., the $FCO_2$ curve, as accurately as possible.

Based on Fowler's method, it would be possible to begin at first by determining a straight line, which describes the pattern of the plateau in the third phase P3 of the capnogram or of the $FCO_2$ curve as accurately as possible. Volume measured values, which describe the starting point and end point of such a straight line, must be determined for this. The volume measured value (final volume) belonging to the end point of the straight line is set with the last value recorded for the expiration process. However, a volume measured value (initial volume) that can be considered for a starting point of the straight line, is, as it were, in the middle of the diagram and is not set at first in any way.

Provisions are therefore made for the automatic approximation of at least part of the curve of the concentration measured values over the volume measured value to determine three straight lines, which follow each other and describe the curve of the measured values as accurately as possible. The formulation in which one or more straight lines are fitted to the measured values or the $FCO_2$ curve will also be described below as an alternative for the formulation of the most accurate description possible of the measured values or $FCO_2$ curve or a part thereof by one or more straight lines. When the term $FCO_2$ curve is used here and hereinafter, it means any set of measured values that go back to an indicator of the carbon dioxide concentration, i.e., for example, also a curve that does not go back directly to a measured carbon dioxide concentration but to measured values for a carbon dioxide partial pressure.

In general, a straight line can be expressed, as is known, in the Cartesian system of coordinates by a linear equation, whose general form is $$y=m+nx,$$

in which n is the slope of the straight line and m is the y axis intercept of the straight line, i.e., the point at which the straight line interests the ordinate of the system of coordinates.

A straight line with the linear equation shown above is defined by all points x, y.

Three straight lines, which adjoin each other but are separate each in itself, are to be fitted to the $FCO_2$ curve in this situation, so that a limited range of validity is thus obtained. Each of the straight lines being sought shall be defined only for the first, second or third phase P1, P2, P3 of the $FCO_2$ curve. The values V0 and V1 are correspondingly set as starting and end volume values of the first straight line for the first phase P1, the values V1 and V2 are set as initial and end volume values of the second straight line for the second phase P2, and the values V2 and V3 are set as initial and end volume values of the third straight line for the third phase. At least the volume values V1 and V2 are now to be determined by a suitable automatic determination.

The corresponding functional equations of the three straight lines are:

Straight line for the first phase P1 (first straight line) with a range of validity of V=V0 ... V1:

$$FCO_2=F0+(V-V0)*(F1-F0)/(V1-V0)$$

Straight line for the second phase P2 (second straight line) with a range of validity of V=V1 ... V2:

$$FCO_2=F1+(V-V1)*(F2-F1)/(V2-V1)$$

Straight line for the third phase P3 (third straight line) with a range of validity of V=V2 ... V3:

$$FCO_2=F2+(V-V2)*(F3-F2)/(V3-V2)$$

The parameters F0, F1, F2, F3 as well as V1 and V2 of the three linear equations must be determined such that the best possible approximation of the three straight lines to the $FCO_2$ curve is obtained corresponding to the measured values recorded. An optimization algorithm of the type of the Levenberg-Marquardt algorithm (Marquardt, D. W.: *Journal of the Society for Industrial and Applied Mathematics*, Vol. 11 (1963), pp. 431-441) is suitable for this. Improvement of the respective values found for the parameters to be determined, here F0, F1, F2, F3, V1, V2 is successively performed with the respective optimization algorithm, and an evaluation of the quality of the respective parameters found is performed on the basis of the sum of squares of the deviation of the straight line defined by the parameters from the measured value curve to be approximated. The goal is a minimal deviation, e.g., minimization of the respective sum of squares obtained.

Figure 5:
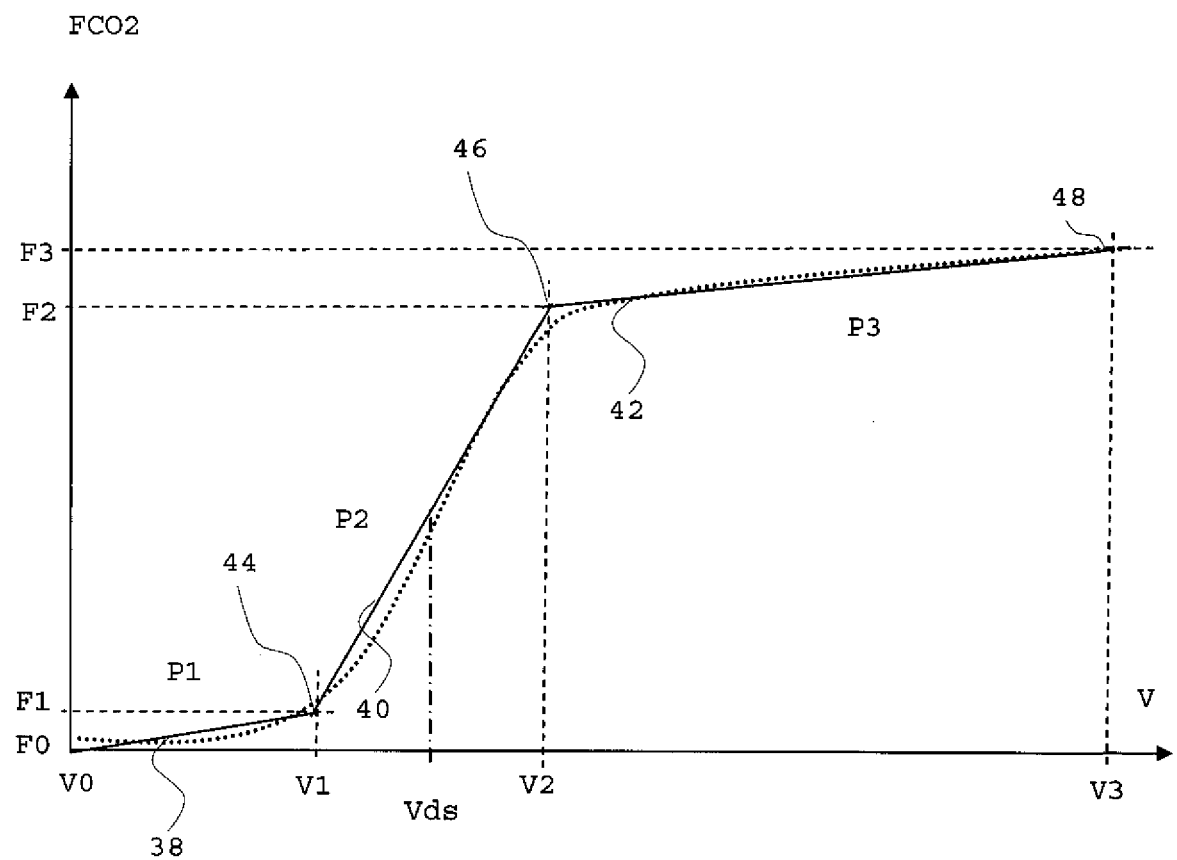
FIG. 5 is a simplified view of a result of an automatic evaluation and analysis of a capnogram.

FIG. 5 shows the result of a fitting of three straight lines, namely, of a first straight line 38 in the first phase P1, of a second straight line 40 in the second phase P2 and of a third straight line 42 in the third phase P3 to the $FCO_2$ curve shown already in FIG. 2. The parameters are checked to determine whether they have meaningful relations to one another; if not, the evaluation of the capnogram is discarded.

The second value pair 46 defines an end point of the second straight line and a starting point of the third straight line 42, i.e., of the third approximated section. Based on the first and second value pairs 44, 46, a first estimated value can be determined according to Fowler for the serial dead space of the lungs of the test subject 14, e.g., as Vds=(V2+V1)/2. The corresponding areas A1 and A2 are determined by numerical integration. Vds is then varied such that A1 becomes equal to A2. A third program code block 50 (FIG. 4) is provided for this evaluation of the measured values recorded subsequent to the analysis of these measured values.

An indicator of the quality of a gas exchange in the lungs of the test subject 14 can be determined, e.g., as $dFCO_2/dV=$ (F3-F2)/(V3-V2), on the basis of the second value pair 46 with the volume measured value V2 and the concentration measured value F2 and of another, last value pair 48, with an end volume measured value V3 and a corresponding concentration measured value F3. A fourth program code block 52 (FIG. 4) is provided for this optional evaluation. The functionality of the third and fourth program code blocks 50, 52 may also be combined.

Figure 6:
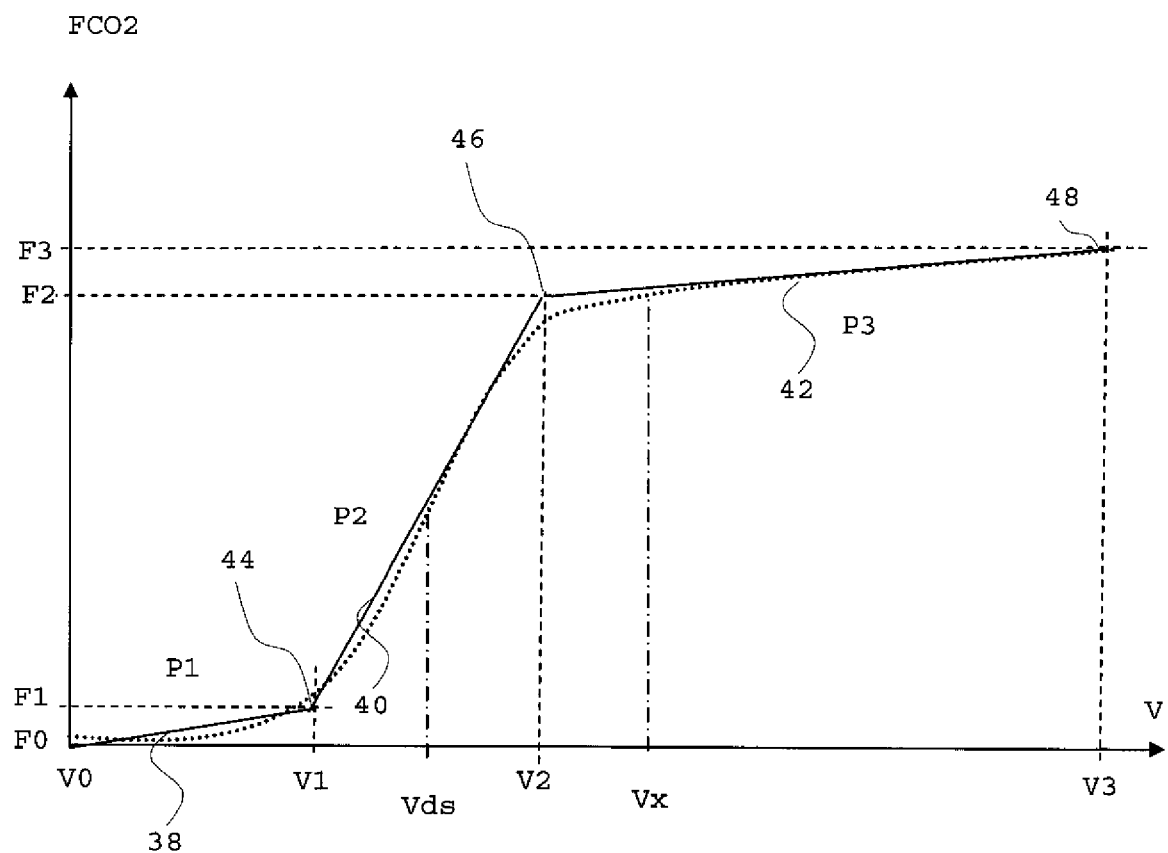
FIG. 6 is a simplified view of an automatic improvement of the result after a first evaluation and analysis step as shown in FIG. 5.

Finally, FIG. 6 shows a possibility of improving the approximation of the third straight line 42. As can be recognized from FIG. 5, the third straight line 42 intersects the measured value curve close to point V2. This intersection is symbolically designated by Vx in FIG. 6. The third straight line 42 can now be approximated anew by taking into account only the volume measured values and corresponding concentration measured values above the intersection Vx. The influence of the inflection point in the measured value curve at V2, which leads to lower values, is now eliminated.

As a partial functionality of the third and/or fourth program code block 50, 52 of the control program 30 (FIG. 4) or in the form of a separate program code block (not shown), the control program 30 comprises program code instructions for actuating the display unit, i.e., e.g., the display screen 32, in order to output the values determined for Vds and/or $dFCO_2/dV$.

The part of the control program 30 shown in FIG. 4 with the first, second, third and fourth program code blocks 34, 36, 50, 52 can be run once, continuously or with a preset or presettable number of repetitions, and interruption by a user is possible in case of a continuous or multiply repeated run. This is represented by the case discrimination block 64, which concludes the structured program in the view in FIG. 4.

Some aspects of the above explanations can be briefly summarized as follows: A method and a device operating according to the method for the automatic evaluation and analysis of a capnogram are provided, wherein measured values for an indicator of an expired volume and measured values for an indicator of a carbon dioxide concentration are recorded for the breathing gas of a test subject 14, wherein the measured values for an indicator of the carbon dioxide concentration—concentration measured values—over the measured values for an indicator of the expired volume—volume measured values—form a basis for an automatic analysis of the measured values recorded, wherein an automatic approximation of at least part of the curve of the concentration measured values over the volume measured values is performed by means of three consecutive straight lines, which divide the curve of the concentration measured values over the volume measured values into approximated first, second and third sections, wherein the third straight line is used as a limiting straight line for the determination of the serial dead space according to Fowler and by taking the mean volume of the second straight line as the first estimated value for Vds.

While specific embodiments of the invention have been shown and described in detail to illustrate the application of the principles of the invention, it will be understood that the invention may be embodied otherwise without departing from such principles.

LIST OF REFERENCE NUMBERS

10 Device
12 Line unit
14 Test subject
16 Sensor
18 Sensor
20 Analysis unit
22 Memory
24 Processing unit
26 Data storage area
28 Program memory area
30 Control program
32 Display screen
34 First program code block
36 Second program code block
38 First straight line
40 Second straight line
42 Third straight line
44 First value pair
46 Second value pair
48 Last value pair
50 Third program code block
52 Fourth program code block
54 Case discrimination block

What is claimed is:

1. A method for the automatic evaluation and analysis of a capnogram in a test subject, the method comprising the steps of:

providing a line unit supplying and receiving breathing gas;

flowing breathing gas into and out of the test subject through the line unit;

providing a first sensor connected to the line unit for detecting gas volume received from the patient;

providing a second sensor connected to the line unit for detecting carbon dioxide concentration in the gas volume;

recording measured values for an indicator of an expired volume and measured values for an indicator of a carbon dioxide concentration for the breathing gas of the test subject;

forming, using a processor, a basis for an automatic analysis of the measured values recorded from the measured values for an indicator of the carbon dioxide concentration—concentration measured values—over the measured values for an indicator of the expired volume—volume measured values including an $FCO_2$ curve;

performing, using the processor, an automatic approximation of at least part of the curve of the concentration measured values over the volume measured values;

using three mutually adjacent straight lines for the approximation;

performing, using the processor, an equal area determination to determine serial dead space (Vds) by means of a third of the three straight lines as a straight line through a plateau of phase 3 of the $FCO_2$ curve;

determining, using the processor, a slope of the third straight line;

determining and indicating, using the processor, a quality of a gas exchange in the lungs of the test subject on the basis of the slope of the third straight line;

determining, using the processor, parameters of the curve of the concentration measured values over the volume measured values which indicate usability of the measured values for determining serial dead space; and automatically estimating, using the processor, usability of the measured values on the basis of the parameters determined.

2. A method in accordance with claim 1, further comprising:

determining a difference between an end volume measured value and the volume measured value belonging to a second value pair;

comparing the difference to a preset or presettable threshold value;

automatically evaluating, as a lack of quality of the approximation or lack of usability of the measured values, when the difference is below a preset or presettable threshold value.

3. A non-transitory storage medium comprising a control program with program code instructions executable by a computer or a processing unit for implementing a method comprising the steps of:

performing artificial respiration on a test subject;

recording measured values for an indicator of an expired volume and measured values for an indicator of a carbon dioxide concentration for breathing gas of the test subject;

forming a basis for an automatic analysis of the measured values recorded from the measured values for an indicator of the carbon dioxide concentration—concentration measured values—over the measured values for an indicator of the expired volume—volume measured values including an $FCO_2$ curve;

performing an automatic approximation of at least part of the curve of the concentration measured values over the volume measured values;

using three mutually adjacent straight lines for the approximation;

performing an equal area determination to determine serial dead space (Vds) by means of the third straight line as a straight line through a plateau of phase 3 of the $FCO_2$ curve;

determining a slope of the third straight line;

determining and indicating a quality of a gas exchange in the lungs of the test subject on the basis of the slope of the third straight line;

determining parameters of the curve of the concentration measured values over the volume measured values which indicate usability of the measured values for determining serial dead space; and automatically estimating usability of the measured values on the basis of the parameters determined.

4. A non-transitory storage medium in accordance with claim 3, wherein the method further comprises:

determining a difference between an end volume measured value and the volume measured value belonging to a second value pair;

comparing the difference to a preset or presettable threshold value; and automatically evaluating, as a lack of quality of the approximation or lack of usability of the measured values, when the difference is below a preset or presettable threshold value.

5. A method for evaluation and analysis of a capnogram for a test subject, the method comprising the steps of:

providing a line unit supplying and receiving breathing gas;

flowing the breathing gas into and out of the test subject through the line unit;

providing a first sensor connected to the line unit for detecting gas volume received from the patient;

providing a second sensor connected to the line unit for detecting carbon dioxide concentration in the gas volume;

collecting expired breathing gas from the test subject and flowing the expired breathing gas through the line unit to the first and second sensors;

detecting a plurality of measured values of the gas volume and the carbon dioxide concentration of the expired breathing gas from the first and second sensors;

forming, using a processor, the plurality of measured values of the detected gas volume and carbon dioxide concentrations into the capnogram with phase 1, 2 and 3 portions;

performing, using the processor, an automatic approximation of three straight lines to the phase 1, 2 and 3 portions of the capnogram;

determining, using the processor, a serial dead space volume of the test subject by performing an equal area determination using the third straight line through the plateau of phase 3 of the capnogram; and determining, using the processor, if the quality of the measured values is sufficient to determine the serial dead space based on an analysis of whether relations of parameters of the approximation are permissible.

6. A method in accordance with claim 5, wherein:

said flowing of breathing gas gases is performed on a test subject to provide artificial respiration.

7. A method in accordance with claim 5, wherein:

said determining if the quality of the measured values is sufficient, is performed by comparing the parameters with a preset threshold value.

8. A method in accordance with claim 5, wherein:

one of said parameters is the volume value at the intersection of the second and third lines;

another of said parameters is the volume value at the end of the third line;

a difference between said one parameter and said another parameter is determined;

said determining if the quality of the measured values is sufficient, is performed by determining if said difference is below a predetermined threshold value.

9. A method in accordance with claim 5, wherein:
the third straight line is determined anew by using a left-hand, first intersection of the straight line with the curve as a new left-hand initial volume value for a repeated fit of the third straight line.

10. A method for the automatic evaluation and analysis of a capnogram in a test subject, the method comprising the steps of:
   providing a line unit supplying and receiving breathing gas;
   flowing breathing gas into and out of the test subject through the line unit;
   providing a first sensor connected to the line unit for detecting gas volume received from the patient;
   providing a second sensor connected to the line unit for detecting carbon dioxide concentration in the gas volume;
   recording measured values for an indicator of an expired volume and measured values for an indicator of a carbon dioxide concentration for the breathing gas of the test subject;
   forming, using a processor, a basis for an automatic analysis of the measured values recorded from the measured values for an indicator of the carbon dioxide concentration—concentration measured values—over the measured values for an indicator of the expired volume—volume measured values including an $FCO_2$ curve;
   performing, using the processor, an automatic approximation of at least part of the curve of the concentration measured values over the volume measured values;
   using three mutually adjacent straight lines for the approximation;
   performing, using the processor, an equal area determination to determine serial dead space (Vds) by means of a third of the three straight lines as a straight line through a plateau of phase 3 of the $FCO_2$ curve; and
   determining anew, using the processor, the third straight line by using a left-hand, first intersection of the straight line with the $FCO_2$ curve as a new left-hand initial volume value for a repeated fit of the third straight line.

* * * * *